(12) United States Patent
Alqahtani et al.

(10) Patent No.: US 9,459,223 B1
(45) Date of Patent: Oct. 4, 2016

(54) METHOD FOR CHEMICAL VAPOR IDENTIFICATION USING SWELLING-BASED SENSORS

(71) Applicant: KING SAUD UNIVERSITY, Riyadh (SA)

(72) Inventors: Hadi Rasam Alqahtani, Riyadh (SA); Martin F. Grell, Sheffield (GB)

(73) Assignee: KING SAUD UNIVERSITY, Riyadh (SA)

(*) Notice: Subject to any disclaimer, the term of this patent is extended or adjusted under 35 U.S.C. 154(b) by 0 days.

(21) Appl. No.: 14/882,359

(22) Filed: Oct. 13, 2015

(51) Int. Cl.
*G01N 25/18* (2006.01)
*G01N 27/12* (2006.01)
*G01N 33/00* (2006.01)

(52) U.S. Cl.
CPC ........ *G01N 27/127* (2013.01); *G01N 33/0016* (2013.01); *G01N 33/0036* (2013.01)

(58) Field of Classification Search
None
See application file for complete search history.

(56) References Cited

U.S. PATENT DOCUMENTS

| 7,501,091 | B2 | 3/2009 | Munoz et al. | |
| 2008/0025876 | A1* | 1/2008 | Ramamurthy | G01N 27/126 422/88 |

OTHER PUBLICATIONS

Bradford et al. latent Heats of Vaporization of Hydrocarbons, 1967, Journal of Chemical and Engineering Data, vol. 12(3), pp. 373-376.*

* cited by examiner

*Primary Examiner* — Robert Xu
(74) *Attorney, Agent, or Firm* — Richard C. Litman

(57) ABSTRACT

The method for chemical vapor identification using swelling-based sensors uses an apparatus that having a first gas chamber including a gas inlet port for inletting a hydrocarbon vapor to be analyzed; a second gas chamber having a hydrocarbon vapor outlet port for exiting the vapor; a chemical sensor placed inside the first and the second gas chambers; and a thermometer placed inside the first and the second gas chambers for measuring the internal temperature; wherein the second gas chamber is placed at a lower temperature compared with the first chamber; and wherein the first gas chamber is in communication with the second chamber by a pipe for transmitting the hydrocarbon vapor from the first chamber to the second chamber.

5 Claims, 5 Drawing Sheets

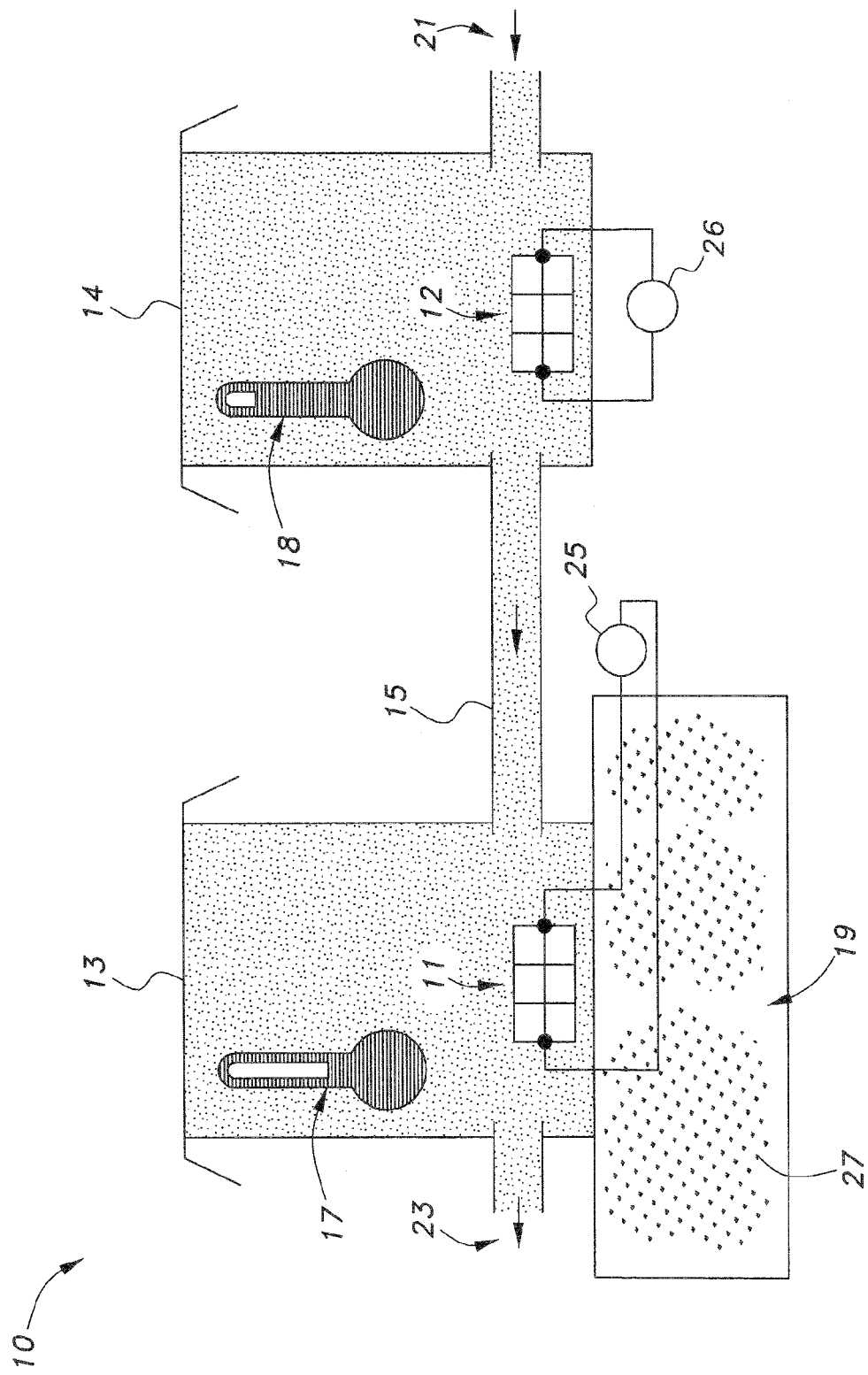

METHOD FOR CHEMICAL VAPOR IDENTIFICATION USING SWELLING-BASED SENSORS

BACKGROUND OF THE INVENTION

1. Field of the Invention

The present invention relates to chemical sensors, and particularly to a method for chemical vapor identification using swelling-based sensors (chemiresistors).

2. Description of the Related Art

Chemiresistors are a class of chemical sensors wherein the electrical resistance of a sensing element changes in response to the presence or absence of a chemical species. Chemiresistors are attractive for use as chemical sensors, since it is relatively easy to measure and record small changes in electrical resistance. Swelling-based chemiresistor sensors use composites, typically, thin films of an electrically insulating matrix, filled with conductive particles. Sensitivity to analytes results from the swelling of the matrix (usually a polymer thin film) in the presence of analyte vapors, a consequential increase in the separation of conductive particles and a resulting increase of electrical resistance, R, or, decrease of conductance, G, which is monitored readily. The traditional implementation of swelling-based vapor sensors are insulating polymers filled with carbon black (CB) particles. Selectivity is due to the choice of insulating matrix, as matrices will swell most in vapors of similar polarity and polarizability, which is quantified by the Hildebrand parameter ($\delta$).

For example, to distinguish between a range of solvent vapors, as in U.S. Pat. No. 5,571,401, issued Nov. 5, 1996 to Lewis et al., an array of chemiresistors was prepared using different polymer matrices, most of which were rather polar (high $\delta$). Solvents were identified by careful analysis of the response pattern of the array. The use of an array of generic sensors with subsequent analysis of response pattern as a broad-range vapor identification system is akin to mammalian olfaction systems (noses), albeit these do not use swelling-based chemiresistors.

More recently, the concept of swelling-based sensors has been extended to films of core/shell nanoparticles (CSNPs), e.g., using organothiol ligand shells coupled to gold nanoparticle cores via Au/thiol coupling. Although such films work as swelling-based gas sensors with good response to alkane and other vapors, it cannot discriminate well between different alkanes. Similarly, the commercially established 'pellistor' catalytic sensors are sensitive to all flammable gases, thus warning of explosion hazards, but it is without the ability to discriminate between different alkanes. Even large arrays of swelling-based sensors cannot discriminate well between chemically similar vapors, more precisely, vapors with similar Hildebrand parameter. However, as swelling is a generic interaction, discrimination between different vapors with swelling-based sensors poses a challenge.

Thus, a method for chemical vapor identification using swelling-based sensors solving the aforementioned problems is desired.

SUMMARY OF THE INVENTION

The method for chemical vapor identification using swelling-based sensors uses an apparatus that comprises a first gas chamber comprising a gas inlet port for inletting a hydrocarbon vapor to be analyzed; a second gas chamber comprising a hydrocarbon vapor outlet port for exiting the vapor; a chemical sensor placed inside the first and the second gas chambers; and a thermometer placed inside the first and the second gas chambers for measuring the internal temperature; wherein the second gas chamber is placed at a lower temperature compared with the first chamber; and wherein the first gas chamber is in communication with the second chamber by a pipe for transmitting the hydrocarbon vapor from the first chamber to the second chamber.

The method of identifying the chemical vapor includes determining the enthalpy of vaporization the analyte by measuring the relative response of the swelling of the two chemical sensors placed inside the above apparatus upon contact of the hydrocarbon with the chemical sensors at different temperatures; and plotting the relative responses of the two chemical sensors over time to determine the enthalpy of vaporization of the hydrocarbon. The identity of the vapor can be identified by reference tables that provide the known enthalpy of vaporization for different compounds.

These and other features of the present invention will become readily apparent upon further review of the following specification and drawings.

BRIEF DESCRIPTION OF THE DRAWINGS

FIG. 1 shows an overview of an apparatus for implementing the method for chemical vapor identification using swelling-based sensors according to the present invention.

Similar reference characters denote corresponding features consistently throughout the attached drawings.

DETAILED DESCRIPTION OF THE PREFERRED EMBODIMENTS

Figure 2A:
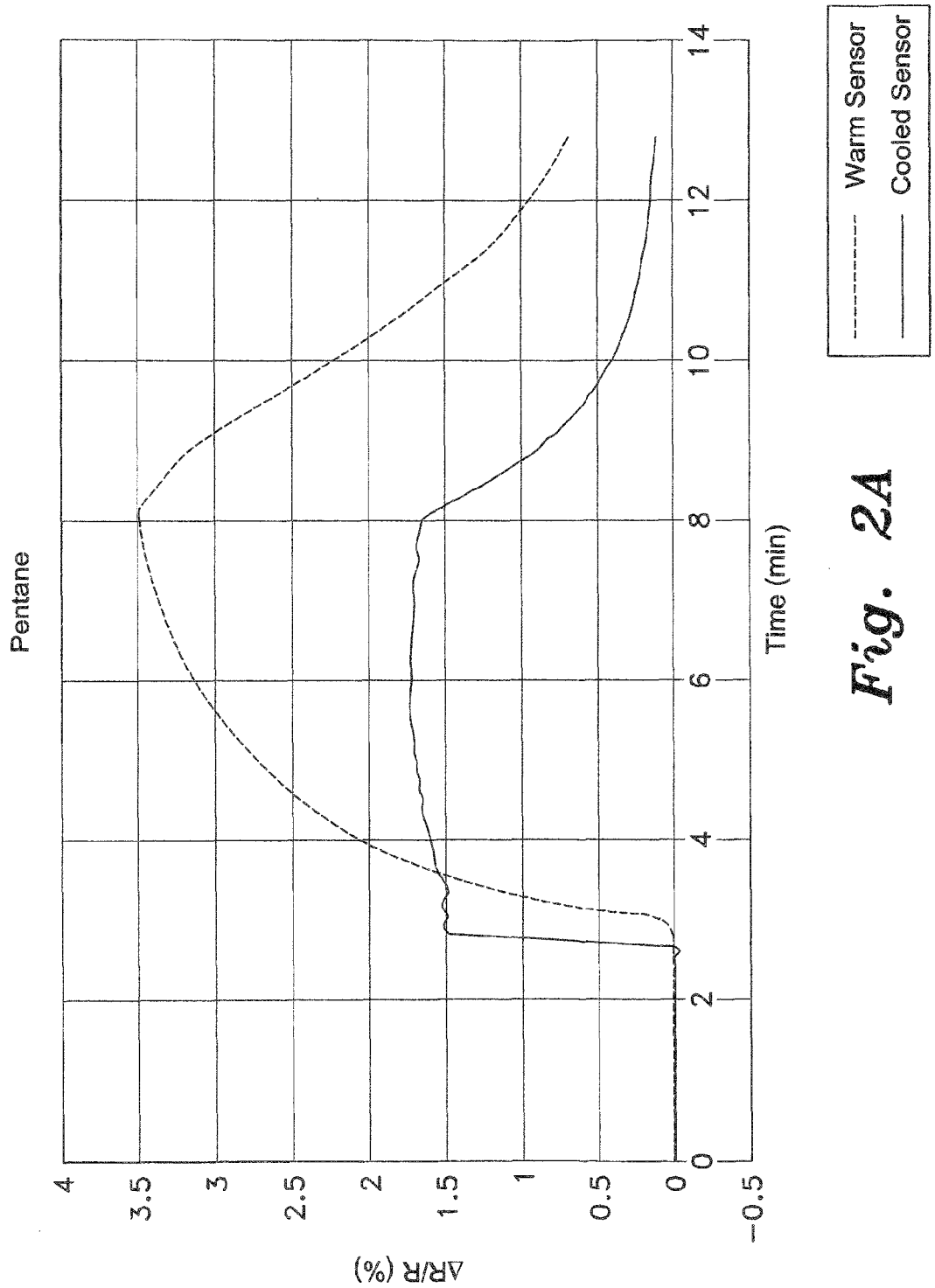
FIG. 2A is a plot showing the ratio of the change in resistance of the swelling-based sensor to the initial resistance as a function of time for sensors in the warm chamber and the cold chamber for pentane.

The vapors of different chemical vapors can be distinguished with generic swelling-based sensors by measuring the vapors' different enthalpies of vaporisation, $\Delta H_v$. The $\Delta Hv$ of a vapor can be calculated from the responses of two nominally identical sensors held at different temperatures inside a gas chamber. While the Hildebrand parameter, $\delta$, and chemical behaviors of different alkanes are very similar to each other, the $\Delta H_v$ of a 'heavy' alkane may be double that of a light one. In this way, it is possible to readily discriminate different alkane vapors with swelling-based sensors, and more generally, open up a new dimension for vapor identification with 'artificial noses'.

An apparatus for identifying the chemical vapor comprises a first gas chamber comprising a gas inlet port for inletting the gas vapor; a second gas chamber comprising a gas outlet port for exiting the vapor; at least one chemical sensor placed inside the first and the second gas chambers;

and at least one thermometer placed in the first and the second gas chambers for measuring the internal temperature. The second gas chamber is placed at a lower temperature compared with the first chamber; and the first gas chamber is in communication with the second chamber by a pipe for transmitting the vapor from the first chamber to the second chamber. The sensor can be a thin film swelling-based sensor, which can comprise gold nanoparticles coated with hexane thiols. The second gas chamber is typically maintained at a temperature of about 20° C. whereas the first gas chamber is maintained at a temperature of about 6° C. using an ice bath.

The method of determining the enthalpy of vaporization of hydrocarbon comprises measuring the relative response of the swelling of the two chemical sensors placed inside the above apparatus upon contact of the hydrocarbon with the chemical sensors at different temperatures, and plotting the relative responses of the two chemical sensors over time to determine the enthalpy of vaporization of the hydrocarbon. The method further comprising comparing the enthalpy of vaporization against known values for hydrocarbons, wherein the hydrocarbon is an n-alkane and wherein the sensors are held at different temperatures.

The ratio of the relative responses of the same or an identical swelling-based sensor under the same concentration of the same vapor, but determined at two different temperatures, is quantitatively predictable by a simple equation that only involves constants, the two temperatures, and the enthalpy of vaporization of the vapor. Conversely, if the ratio of the simultaneous responses of a nominally identical pair of swelling-based sensors held at two known, different temperatures under exposure to an unknown vapor is known, the same simple equation allows for the calculation of the vapor's enthalpy-of-vaporization ($\Delta H_v$), independent of the concentration of the vapor. The following examples will further illustrate chemical vapor identification using swelling-based sensors.

When a pair of nominally identical swelling-based sensors is held at different temperatures, their different responses to the same vapor allow for calculation of the vapor's enthalpy of vaporization. Enthalpies may differ significantly for vapors with very similar Hildebrand parameters. Using only two generic swelling-based sensors, it is possible to clearly distinguish between vapors of different chemical vapors. Typically, the swelling-based sensor is a set of pairs (possibly a single pair) of nominally identical, swelling-based sensors. FIG. 1 shows the configuration of an apparatus 10 for vapor identification. The sensors 11, 12 are made of gold nanoparticles coated with hexane thiols for stabilization and deposited using Langmuir-Shaefer method on a patterned substrate with built-in interdigitated gold electrodes. The first sensor 12 is placed in a first gas chamber 14, and the second sensor 11 is placed in a second gas chamber 13. The two chambers 13, 14 are connected in series by a pipe 15. The two chambers 13, 14 have a temperature difference $\Delta T$. A thermometer 17, 18 is placed in each chamber 13, 14, respectively, for in-situ temperature measurement. The second chamber 13 was placed in an ice bath 19 having, for example, crushed ice 27 for obtaining a temperature difference sufficient for doing the identification experiments. The chemical vapor with precise concentration is controlled by a mass flow controlling unit. The chemical vapor to be identified travels through the inlet 21 and through the first chamber 14 into the second chamber 13 before exiting out through an outlet port 23. For resistance measurements, each sensor 11, 12 is connected to a respective Fluke Ohmmeter 25, 26 in FIG. 1, which is kept outside the respective gas chamber 13, 14.

Figure 2B:
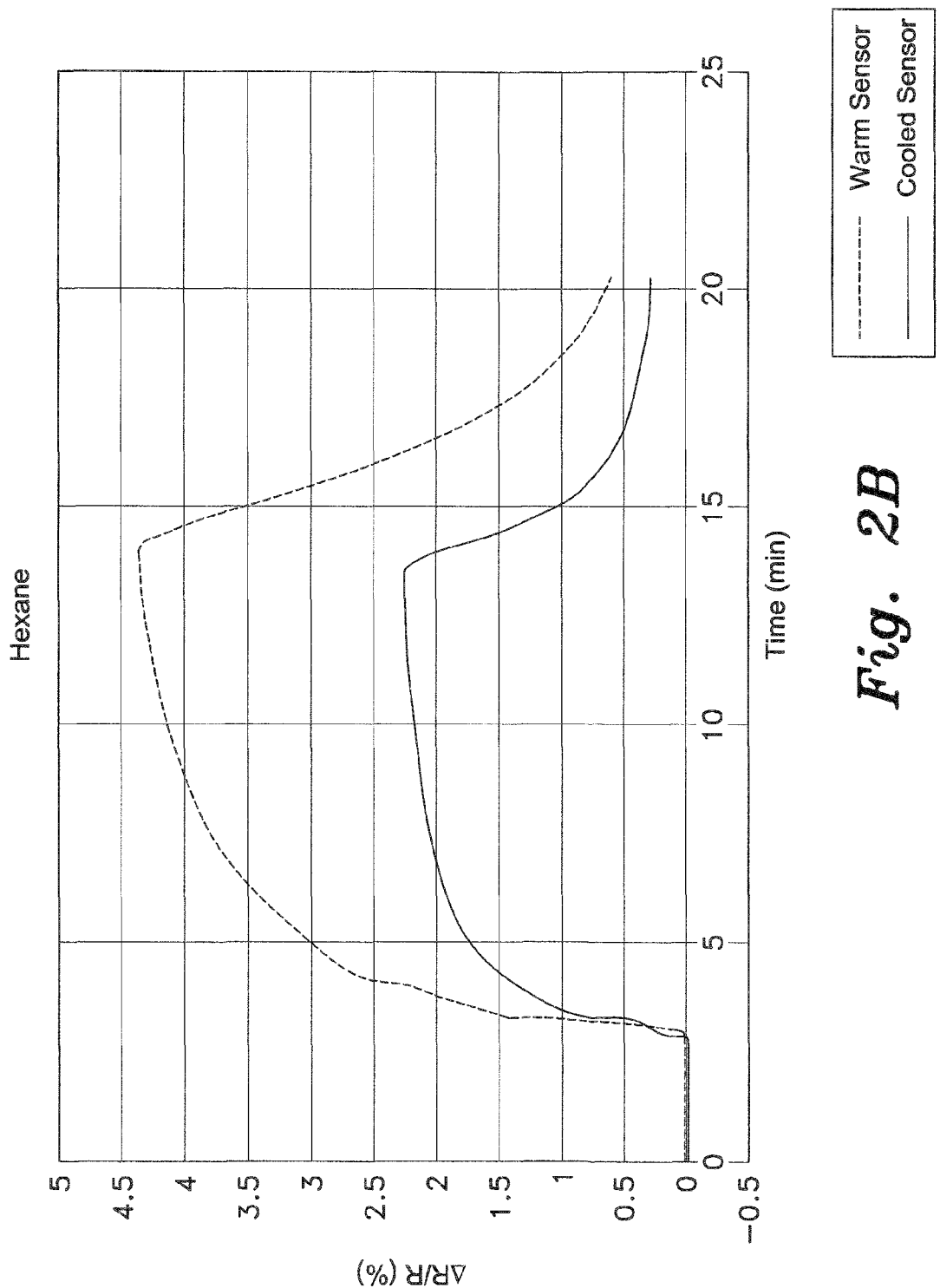
FIG. 2B is a plot showing the ratio of the change in resistance of the swelling-based sensor to the initial resistance as a function of time for sensors in the warm chamber and the cold chamber for hexane.
Figure 2C:
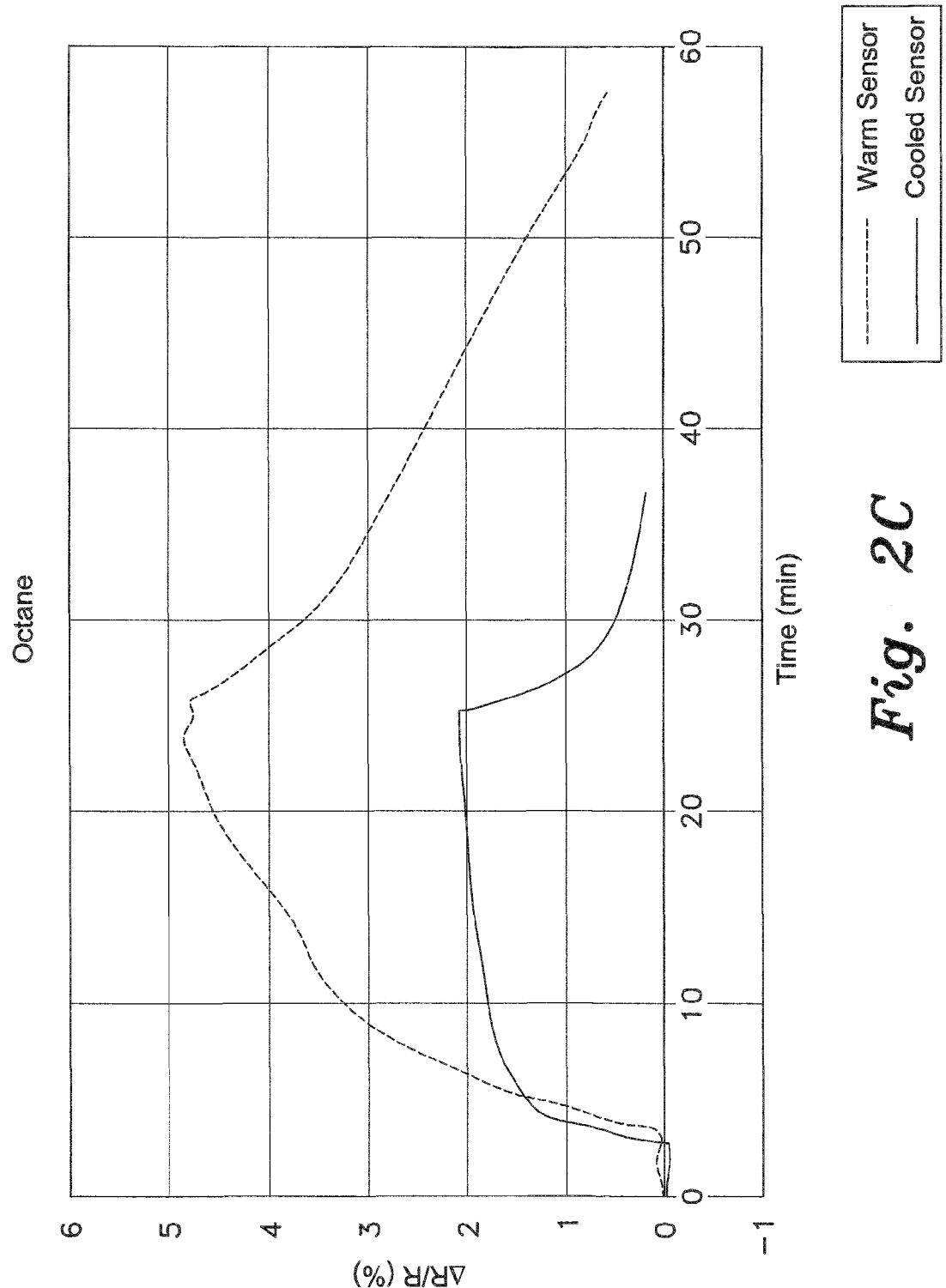
FIG. 2C is a plot showing the ratio of the change in resistance of the swelling-based sensor to the initial resistance as a function of time for sensors in the warm chamber and the cold chamber for octane.
Figure 2D:
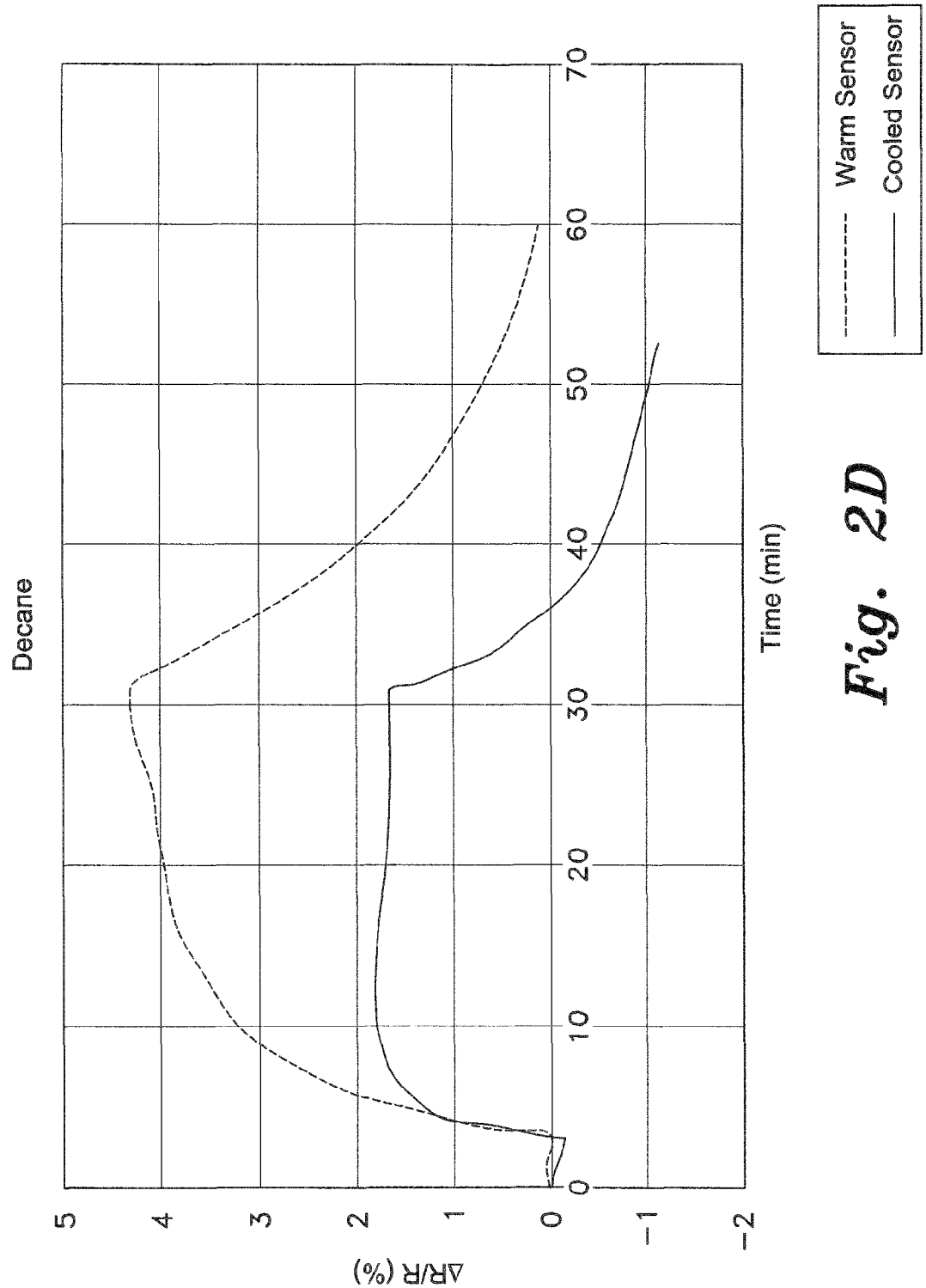
FIG. 2D is a plot showing the ratio of the change in resistance of the swelling-based sensor to the initial resistance as a function of time for sensors in the warm chamber and the cold chamber for decane.

For a proof of concept, the inventors have conducted vapor identification experiments for some n-alkanes. FIGS. 2A-2D show the discrimination experiments of four tested n-alkane vapors: (a) pentane, (b) hexane, (c) octane, and (d) decane. There are two distinctive loops taken simultaneously at two different temperatures: room temperature (warm sensor, denoted by solid line) and at 6° C. (cooled sensor, depicted by dotted line). The responses of the warm sensors $\Delta R/R$ (red) and the cooled sensor $\Delta R/R$ (blue) of a pair of nominally identical chemiresistors under exposure/recovery cycles to 10% $p_{sat}$ atmospheres of each analyte as a function of time are shown in the drawings. The warm sensor was kept at $T_W \sim 20°$ C., whereas the cooled sensor was kept at $T_C \sim 6°$ C. It was observed that each analyte shows an approximately exponential rise in response after the start of exposure that reaches a saturation level, and an approximately exponential drop back to the original baseline under $N_2$ purge after the end of vapor exposure.

The sensitivity (S) of each sensor was calculated according to the formula of Lewis et al.:

$$S = \frac{\Delta R/R_o}{P/P_{sat}} = \frac{(R_{sat} - R_o)/R_o}{P/P_{sat}}, \quad (1)$$

where $\Delta R/R_o$ is the response of the sensor to an analyte, $R_{sat}$ and $R_o$ are the saturation and initial resistances, respectively, and $P/P_{sat}$ is the analyte vapor pressure P normalised by the saturation vapor pressure $P_{sat}$.

The enthalpy of vaporization ($\Delta H_V$) can be calculated for each vapor as follows:

$$\Delta H_V = R\ln(f) \Big/ \left(\frac{1}{T_C} - \frac{1}{T_W}\right), \quad (2)$$

where R=8.314 J/mole.K is the gas constant, f is the sensitivity of the cooled sensor ($S_c$) divided by the sensitivity of the warm sensor ($S_w$): f=$S_c/S_w$, and $T_C$ and $T_W$ are the temperatures at which the cooled and warm sensors are kept, respectively.

Table 1 summarizes the relevant data taken from FIGS. 2A-2D, the calculated ln(f) and $\Delta H_V$ (designated $\Delta H_V$(exp.)) for all alkanes used here, and the literature values for $\Delta H_V$ (designated $\Delta H_V$(lit.)) for comparison. Table 1 illustrates in the example of the n-alkanes ('linear' alkanes) how chemically similar vapors can be discriminated with generic swelling-based chemiresistors, when pairs of chemiresistors held at different temperatures are used. Focusing on swelling at ambient temperature ($T_W$) alone does not allow such discrimination. It was observed that the values for sensitivities at ambient temperature are similar for all alkanes, in agreement with previous studies.

TABLE 1

Experimental results

| Vapor | $T_W$ [K] | $T_C$ [K] | $S_w$ | $S_c$ | ln(f) | $\Delta H_V$ (exp.) [kJ/mol] | $\Delta H_V$ (lit) [kJ/mol] |
|---|---|---|---|---|---|---|---|
| n-pentane | 295 | 279 | 0.173 | 0.349 | 0.7 | 26.8 | 26.4 |
| n-hexane | 292 | 279 | 0.225 | 0.436 | 0.662 | 34.4 | 31.5 |
| n-octane | 293.5 | 279 | 0.200 | 0.476 | 0.867 | 40.7 | 41.5 |
| n-decane | 292 | 279 | 0.18 | 0.430 | 0.87 | 48.9 | 51.4 |

By including data from chemiresistors cooled with respect to ambient temperature and quantitative evaluation of the resulting sensitivity enhancement, it is possible to distinguish alkanes by comparison of calculated enthalpies of vaporization ($\Delta H_v$) to literature values. The calculated $\Delta H_V$ are clearly different from each other, but all match the literature value for the respective alkane within the margin of error. Thus, the precise chemical identity of an unknown n-alkane vapor can be determined with the help of measured swelling data from pairs of core/shell nanoparticle (CSNP) chemiresistors held at different temperatures. This includes distinguishing n-alkanes different by only one carbon, for example, (pentane vs. hexane), which is otherwise very difficult.

The apparatus and method described here thus adds another independent dimension to vapor identification systems. This is most clearly understood when considering that the degree of swelling of different matrices is controlled by the matching or mismatching of vapor and matrix Hildebrand parameters, $\delta$, while the increase or decrease of swelling by cooling or heating is controlled by a property of the vapor alone. Arrays narrow down Hildebrand parameter, while pairs held at different temperature narrow down the enthalpy of vaporization. When combined, by running two nominally identical sensor arrays in parallel, but held at different temperatures, it is possible to narrow down the identity of unknown vapors to a small area in the ($\delta$, $\Delta H_V$) plane, rather than only to a range on the $\delta$ scale (as for an array), or only to a range on the $\Delta H_V$ scale (as for pairs kept at different temperature).

Therefore, the described method will give much richer information to be fed into analysis schemes for vapor identification from the data of generic sensors, potentially with a smaller number of sensors in total than previous methods.

It is to be understood that the present invention is not limited to the embodiments described above, but encompasses any and all embodiments within the scope of the following claims.

We claim:

1. A method for chemical vapor identification of an unknown hydrocarbon analyte vapor using swelling-based sensors, comprising the steps of:

providing an apparatus for identifying the unknown hydrocarbon analyte vapor, the apparatus comprising:
a first gas chamber comprising a gas inlet port for inletting the unknown hydrocarbon analyte vapor to be analyzed;
a second gas chamber comprising an outlet port for exiting the unknown hydrocarbon analyte vapor;
a first chemical sensor disposed inside the first gas chamber and a second chemical sensor disposed inside the second gas chamber;
first and second thermometers disposed inside the first and the second gas chambers, respectively; and
a pipe connecting the first chamber to the second chamber in series thereby providing simultaneous fluidic communication between the first and second chambers;

maintaining the unknown hydrocarbon analyte vapor in the first chamber having the first chemiresistor disposed therein until the first chemiresistor is saturated with the unknown hydrocarbon analyte vapor at a first temperature, wherein the first temperature is approximately 20° C.;

maintaining the unknown hydrocarbon analyte vapor in the second chamber having the second chemiresistor disposed therein until the second chemiresistor is saturated with the unknown hydrocarbon analyte vapor while maintaining the second chamber at a second temperature colder than the first temperature;

calculating the sensitivity of the first chemiresistor and the second chemiresistor simultaneously at the different temperatures;

calculating the enthalpy of vaporization of the unknown hydrocarbon analyte from the sensitivities of the first and second chemiresistors and the first and second resistors;

comparing the calculated enthalpy of vaporization of the unknown hydrocarbon analyte with published literature values of the enthalpy of vaporization of known hydrocarbon compounds; and identifying the analyte hydrocarbon vapor as a known hydrocarbon compound when the calculated and published enthalpies of vaporization are substantially the same.

2. The method for chemical vapor identification according to claim 1, wherein maintaining the second chamber at a second temperature colder than the first temperature comprises at least partially immersing the second chamber in an ice bath.

3. The method for chemical vapor identification according to claim 1, wherein the second temperature is about 6° C.

4. The method for chemical vapor identification according to claim 1, wherein said step of calculating the sensitivity of the first chemiresistor and the second chemiresistor comprises the step of solving the following equation for each of the chemiresistors:

$$S = \frac{\Delta R / R_o}{P / P_{sat}} = \frac{(R_{sat} - R_o)/R_o}{P / P_{sat}},$$

where $\Delta R/R_o$ is a response of the chemiresistor to the analyte, $R_{sat}$ and $R_o$ are the saturation and initial resistances, respectively, and $P/P_{sat}$ is the analyte vapor pressure P normalised by $P_{sat}$, the vapor pressure in the chamber when the chemiresistor is saturated with the analyte vapor.

5. The method for chemical vapor identification according to claim 4, wherein said step of calculating the enthalpy of vaporization of the analyte comprises solving the equation:

$$\Delta H_V = R\ln(f) \Big/ \left(\frac{1}{T_C} - \frac{1}{T_W}\right),$$

where R=8.314 J/mole.K is the gas constant, f is the sensitivity of the second chemiresistor ($S_c$) divided by the sensitivity of the first chemiresistor ($S_w$): f=$S_c/S_w$, and $T_C$ and $T_W$ are the second and first temperatures, respectively.

* * * * *